(12) United States Patent
Lau et al.

(10) Patent No.: US 6,454,749 B1
(45) Date of Patent: *Sep. 24, 2002

(54) PERSONAL CARE PRODUCTS WITH DYNAMIC AIR FLOW

(75) Inventors: Jark Chong Lau; James Arthur Davis, both of Roswell; Kenneth Yin Wang; Wanda Walton Jackson, both of Alpharetta, all of GA (US)

(73) Assignee: Kimberly-Clark Worldwide, Inc., Neenah, WI (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/132,386

(22) Filed: Aug. 11, 1998

(51) Int. Cl.$^7$ ........................ A61M 13/15; A61M 13/20
(52) U.S. Cl. .............................. 604/385.12; 604/385.01
(58) Field of Search ............................. 604/358, 385.1, 604/385.2, 387, 385.01, 385.12, 393, 394, 396, 373, 383, 312; 2/DIG. 1, 80, 75, 82; 450/108

(56) References Cited

U.S. PATENT DOCUMENTS

| | | | | |
|---|---|---|---|---|
| 1,261,448 A | * | 4/1918 | Siegel ........................ | 2/DIG. 1 |
| 2,544,069 A | * | 3/1951 | Cutler ........................ | 2/DIG. 1 |
| 2,880,727 A | * | 4/1959 | Whalen ........................ | 2/DIG. 1 |
| 3,150,665 A | * | 9/1964 | May, Jr. et al. ........... | 2/DIG. 1 |
| 4,964,858 A | * | 10/1990 | Livny ....................... | 604/385.1 |
| 5,057,368 A | | 10/1991 | Largman et al. ............ | 428/397 |
| 5,069,970 A | | 12/1991 | Largman et al. ............ | 428/373 |
| 5,108,820 A | | 4/1992 | Kaneko et al. ............. | 428/198 |
| 5,108,827 A | | 4/1992 | Gessner ..................... | 428/219 |
| 5,277,976 A | | 1/1994 | Hogle et al. ............... | 428/397 |
| 5,336,552 A | | 8/1994 | Strack et al. .............. | 428/224 |
| 5,382,400 A | | 1/1995 | Pike et al. ................. | 264/168 |
| 5,520,674 A | * | 5/1996 | Lavon et al. ............... | 604/385.2 |
| 5,582,604 A | * | 12/1996 | Ahr et al. .................. | 604/385.1 |
| 5,769,834 A | | 6/1998 | Reiter et al. | |
| 6,128,784 A | * | 10/2000 | Frank ........................ | 2/DIG. 1 |

OTHER PUBLICATIONS

*Polymer Blends and Composites* by John A. Manson and Leslie H. Sperling, copyright 1976 by Plenum Press, a division of Plenum Publishing Corporation of New York, IBSN 0–306–30831–2, at pp. 273 through 277.

* cited by examiner

Primary Examiner—John G. Weiss
Assistant Examiner—K. M. Reihle
(74) Attorney, Agent, or Firm—Christos S. Kyriakou; James B. Robinson

(57) ABSTRACT

There is provided a bellows adapted to be actuated by the movement of a wearer's body and force air into a personal care product in a region between the skin of the wearer and the product. The bellows may be located in the periphery of the personal care product and the discharge of the bellows is directed into the personal care product so air is forced into the product.

7 Claims, 3 Drawing Sheets

PERSONAL CARE PRODUCTS WITH DYNAMIC AIR FLOW

FIELD OF THE INVENTION

The present invention relates to an air moving structure in an article for personal care like diapers, training pants, swimwear, absorbent underpants, adult incontinence products, bandages and feminine hygiene products.

BACKGROUND OF THE INVENTION

Personal care articles include such items as diapers, training pants, swimwear, bandages, incontinence garments and feminine hygiene products such as sanitary napkins, panty-liners and tampons and the like. The most basic design of all such articles typically includes a bodyside liner, an outer cover and an absorbent core disposed between the bodyside liner and the outer cover. Generally, the bodyside liner and the outer cover are sealed about the periphery so as to encapsulate the absorbent core and thus make it possible to entrap and retain any fluids contained within the absorbent core. Depending upon the design of the particular personal care absorbent article, other components also may be included. Thus, the product may include such things as elastic side panels, fluid containment flaps, fastening devices and other layers of fluid transfer or retention materials.

The lack of air flow into personal care products has been a long standing concern because of adverse skin effects which are believed to be promoted by continuous exposure to moisture and the enzymes and other substances in bodily fluids. Many attempts to correct these adverse effects have been made, including the provision of materials designed to wick and hold liquids away from the skin, or to increase the breathability or air permeability of the personal care product components. Breathable diaper outer covers, for example, have been developed to allow increased air exchange and flow into the product and so improve the environment adjacent the skin. The condition of the wearer's skin is thus an area of continuing concern to the personal care product industry.

In light of low air flow within personal care products, even those with breathable outercovers, it is an object of this invention to provide a dynamically breathable personal care product wherein air is forced into the product to the region between the skin and the product. Dynamic breathability, i.e., the forcing of air into a product, should not be confused with the provision of breathable materials which merely allow air to pass through them in a passive fashion.

It is a further object of this invention to provide a dynamically breathable personal care product wherein the normal movement of the wearer results in the drawing of air into the product, by, for example, the change in the circumference of the wearer's midsection during normal respiration.

SUMMARY OF THE INVENTION

Objects of the invention are achieved by a bellows that is adapted to be actuated by the normal movement of a wearer's body and discharge air into a personal care product in a region between a wearer's skin and the product. The bellows comprises valving means having at least a first one-way valve which intakes air from outside the product and a second one-way valve which discharges air into the product in a region between the wearer's skin and the product. The bellows have sufficient resilience to spring back into shape and refill with air from outside of the product after being compressed by the normal movement of the wearer.

DEFINITIONS

Figure 1:
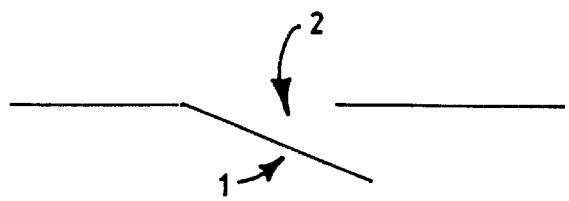
FIG. 1 shows a one way valve.

"Disposable" includes being disposed of after a single use and not intended to be washed and reused.

"Front" and "back" are used throughout this description to designate relationships relative to the garment itself, rather than to suggest any position the garment assumes when it is positioned on a wearer.

"Inward" and "outward" refer to positions relative to the center of an absorbent garment, and particularly transversely and/or longitudinally closer to or away from the longitudinal and transverse center of the absorbent garment.

"Liquid" means a substance and/or material that flows and can assume the interior shape of a container into which it is poured or placed.

"Liquid communication" means that liquid is able to travel from one layer to another layer, or one location to another within a layer.

"Longitudinal" and "transverse" have their customary meaning. The longitudinal axis lies in the plane of the article when laid flat and fully extended and is generally parallel to a vertical plane that bisects a standing wearer into left and right body halves when the article is worn. The transverse axis lies in the plane of the article generally perpendicular to the longitudinal axis. The article as illustrated is longer in the longitudinal direction than in the transverse direction.

"Conjugate fibers" refers to fibers which have been formed from at least two polymers extruded from separate extruders but spun together to form one fiber. Conjugate fibers are also sometimes referred to as multicomponent or bicomponent fibers. The polymers are usually different from each other though conjugate fibers may be monocomponent fibers. The polymers are arranged in substantially constantly positioned distinct zones across the cross-section of the conjugate fibers and extend continuously along the length of the conjugate fibers. The configuration of such a conjugate fiber may be, for example, a sheath/core arrangement wherein one polymer is surrounded by another or may be a side by side arrangement, a pie arrangement or an "islands-in-the-sea" arrangement. Conjugate fibers are taught in U.S. Pat. No. 5,108,820 to Kaneko et al., U.S. Pat. No. 5,336,552 to Strack et al., and U.S. Pat. No. 5,382,400 to Pike et al. For two component fibers, the polymers may be present in ratios of 75/25, 50/50, 25/75 or any other desired ratios. The fibers may also have shapes such as those described in U.S. Pat. No. 5,277,976 to Hogle et al., and U.S. Pat. Nos. 5,069,970 and 5,057,368 to Largman et al., hereby incorporated by reference in their entirety, which describe fibers with unconventional shapes.

"Biconstituent fibers" refers to fibers which have been formed from at least two polymers extruded from the same extruder as a blend. The term "blend" is defined below. Biconstituent fibers do not have the various polymer components arranged in relatively constantly positioned distinct zones across the cross-sectional area of the fiber and the various polymers are usually not continuous along the entire length of the fiber, instead usually forming fibrils or protofibrils which start and end at random. Biconstituent fibers are sometimes also referred to as multiconstituent fibers. Fibers of this general type are discussed in, for example, U.S. Pat. No. 5,108,827 to Gessner. Bicomponent and biconstituent fibers are also discussed in the textbook *Polymer Blends and Composites* by John A. Manson and Leslie H. Sperling, copyright 1976 by Plenum Press, a division of Plenum Publishing Corporation of New York, IBSN 0-306-30831-2, at pages 273 through 277.

"Personal care product" means diapers, training pants, swimwear, absorbent underpants, adult incontinence products, bandages and feminine hygiene products.

"Feminine hygiene products" means sanitary napkins or pads, tampons and panty-liners.

"Target area" refers to the area or position on a personal care product where an insult is normally delivered by a wearer.

Test Methods
Material Caliper (Thickness)

The caliper of a material is a measure of thickness and is measured at 0.05 psi with a STARRET® bulk tester, in units of millimeters.

Density

The density of the materials is calculated by dividing the weight per unit area of a sample in grams per square meter (gsm) by the bulk of the sample in millimeters (mm) at 68.9 Pascals and multiplying the result by 0.001 to convert the value to grams per cubic centimeter (g/cc). A total of three samples would be evaluated and averaged for the density values.

DETAILED DESCRIPTION OF THE INVENTION

Personal care absorbent articles include such items as diapers, training pants, swimwear, feminine hygiene products such as sanitary napkins, panty-liners and tampons, incontinence garments and devices, bandages and the like. The most basic design of all such articles typically includes a bodyside liner, an outer cover and an absorbent core disposed between the bodyside liner and the outer cover.

The air flow into personal care products has been a long standing concern because of adverse skin effects which are believed to be promoted by continuous exposure to moisture, high temperatures and the enzymes and other substances in bodily fluids. Many attempts to correct these adverse effects have been made, including the provision of materials designed to wick and hold liquids away from the skin, or to increase the breathability or air permeability of the personal care product components. Breathable diaper outer covers, for example, have been developed to allow increased air exchange and flow into the product and so improve the environment adjacent the skin.

In light of the low air flow within personal care products, it is an object of this invention to provide a dynamically breathable personal care product wherein air is drawn or forced into the product in the region between the skin and the product. Dynamic breathability, i.e., the forcing of air into a product, should not be confused with the provision of breathable materials which merely allow air to pass through them in a passive fashion.

A personal care product, for example a diaper, typically has a bodyside layer, optionally a fluid transfer layer, a fluid retention layer and a garment side layer. It may also have a distribution layer or other optional layers to provide specialized functions.

The bodyside layer is sometimes referred to as a bodyside liner or topsheet. In the thickness direction of the article, the liner material is the layer against the wearer's skin and so the first layer in contact with liquid or other exudate from the wearer. The liner further serves to isolate the wearer's skin from the liquids held in an absorbent structure and should be compliant, soft feeling and non-irritating.

The bodyside liner can be surface treated with a selected amount of surfactant, such as about 0.2% Ahcovel surfactant, or otherwise processed to impart the desired level of wettability and hydrophilicity. If a surfactant is used, it can be an internal additive or applied to the layer by any conventional means, such as spraying, brush coating and the like, prior to the deposition of the next layer.

The fluid retention layer must absorb liquid from the adjacent bodyside layer in a controlled manner such that liquid may be stored away from contact with the body. Retention materials generally comprise binder, synthetic fibers and natural fibers. While any of the layers of a personal care product may optionally contain a superabsorbent, the fluid retention layer is the most logical layer to contain such a component.

The garment side liner layer, also referred to as a backsheet or outer cover is the farthest layer from the wearer. The outer cover functions to prevent body exudates contained in an absorbent structure from wetting or soiling the wearer's clothing, bedding, or other materials contacting the personal care product. The outer cover has traditionally been formed of a thin thermoplastic film, such as polyethylene film, which is substantially impermeable to liquid but may optionally be composed of a vapor or gas permeable, microporous "breathable" material, that is permeable to vapors or gas yet substantially impermeable to liquid.

The optional fluid transfer layer, also referred to as a surge layer, is most typically interposed between and in intimate, liquid communicating contact with the bodyside liner and another layer such as a fluid distribution or retention layer. The fluid transfer or surge layer allows fluid movement through itself generally in the Z-direction, i.e. away from the bodyside and towards the garment side.

An optional distribution layer may be interposed above (toward a wearer) the fluid retention layer and must be capable of moving fluid from the point of initial deposition to where storage is desired. The fluid distribution layer, therefore, in addition to allowing fluid movement through itself in the Z-direction, also moves fluid in the X and Y directions. Distribution must take place at an acceptable rate such that the target insult area, generally the crotch area, is ready for the next insult. The time between insults can range from just a few minutes to hours, generally depending on the age of the wearer and the personal care product in question.

The breathable outer cover discussed above is an example of the approach which has been used previously to increase the ability of air to enter the product. The breathable outer cover allows air through, and, in bench testing, can provide good air flow rates as measured by conventional ASTM permeability testing. While a breathable outer cover will permit air to flow through, in actual use there is no way to guarantee the flow of air through the product and all the way to the skin, since this method is entirely passive. The dynamic air flow provision remedies this by avoiding the exclusive reliance on passive air entry and forcing or drawing air into the product into the region between the skin and the product.

The heart of the invention is a bellows located in the periphery of the product. One location for the bellows is in the waist area, preferably as high on the product as possible, in, for example, a diaper, training pant or incontinence garment. In the waist location, activation of the bellows is by the normal breathing of the wearer which compresses and releases the bellows with the rise and fall of the wearer's midsection. Another location is in the leg area of, for example, a sanitary napkin, diaper, training pant or incontinence garment. Activation of a bellows in the leg area is by the compression and release of the bellows by the thighs of the wearer as the wearer walks, or while sitting down and getting up. Yet another location for the bellows would be in the periphery of a bandage for wound care where it would be activated by the flexing of the bandage in response to body movement. In a bandage, the amount of air forced into the bandage would, of course, be highly variable, dependent on the location of the bandage on the body. In any case the bellows is located in the periphery of the product.

This invention directs the air driven from the bellows into the rest of the personal care product and across the skin of the wearer. It should be noted that even a small amount of air per compression of the bellows can greatly increase the cumulative air flow through a product since personal care products may be worn for long periods of time. The air driven into the product eventually escapes, of course, either, in the case of a diaper for example, through the leg or torso openings, or through the outercover if it is permeable.

The components of the bellows include an air containment sack or bag, valving means to allow air in and out of the bellows, and a resilient component to make the bellows refill with air.

The air bag may be made out of any suitable air impermeable material. Such materials include polyolefin films and coated nonwoven fabrics. A bag made from polyethylene film would be quite suitable and inexpensive for this application. A nonwoven fabric, for example, a fabric made by the meltblowing process, and coated with a latex layer would also be suitable. Latex would be a good coating candidate because of its inherent flexibility.

Figure 2A:
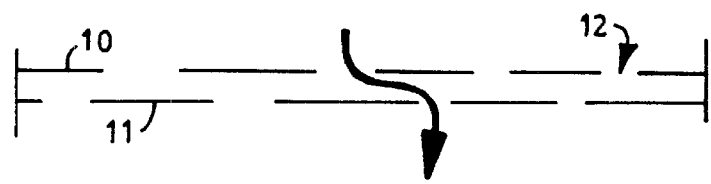
FIG. 2A and 2B show a one way valving mechanism using two pliant sheets in a cross-sectional view.
Figure 2B:
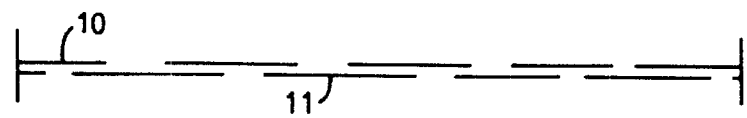

The valving means must allow air into the bag on expansion and direct it into the product upon compression. Air must be drawn into the bag from outside the product to be most effective. At least two one way valves are required to 1) intake air from outside and 2) discharge air into the product. Any suitable one way valve would function in this service and a suitable valve is shown in FIG. 1. In FIG. 1, a pliant flap 1 will be forced to move away from the opening 2 when air flows toward the flap 1 from outside as illustrated by the arrow. If air flow is reversed, the air would force the pliant flap 1 towards opening 2 and close the opening 1. Note that the closing of the opening 2 need not completely seal the bag completely air-tight, as some air may be lost through the same valve it entered. FIGS. 2A and 2B show another valving mechanism wherein two pliant sheets 10, 11 with openings 12 which do not overlap form the valve. Air flow is again shown by the large arrow. FIG. 2A shows the pliant sheets in the open configuration and FIG. 2B shows them in the closed position.

The resilient component of the bellows must be constructed of a flexible material which will have sufficient resiliency or compression resistance to spring back into shape after being compressed by the breathing or leg movement of the wearer. The resilient component of the bellows may be elastic. One suitable material for the resilient component of the bellows is, for example, a corrugated bonded carded web of fibers. Such a material may be between 1 and 4 osy (34–135 gsm) in basis weight and have a density between about 0.01 to 0.03 gm/cc. Fibers for such a material may have a denier between about 3 and 10 dpf and be made from thermoplastics such as polyesters, polyolefins, nylons and the like. Conjugate and biconstituent fibers are also suitable.

Figure 3:
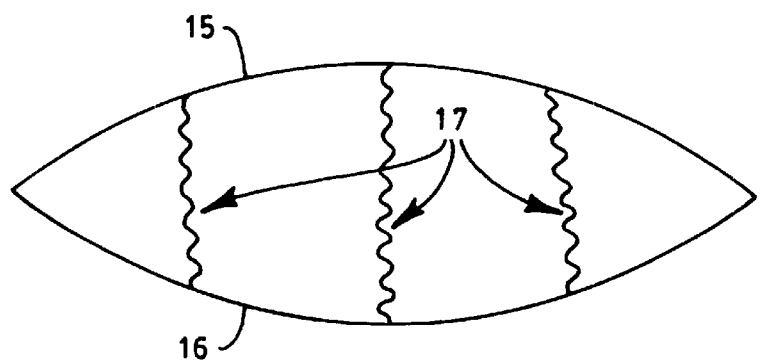
FIG. 3 is a cross-sectional view of a bellows with a resilient component within Each of the outer surfaces of the bellows incorporates a one way valving arrangement (not shown).

The shape and size of the bellows will vary based on the size of the wearer and product and the particular personal care product into which it is incorporated. FIG. 3 shows a bellows having outer surfaces 15, 16 which contain a resilient component 17 between them. Each of the outer surfaces 15, 16 incorporates a one way valving arrangement (not shown).

In the waist location of a diaper, for example, the bellows could be rectangular, oblong or oval and arranged so that the long dimension is across the belly of the wearer while wearing the diaper. The discharge of the bellows into the product may be directly into the waist of the wearer, or, to increase the amount of air going deeper into the product, can be directed by some distribution means, e.g. tubes or piping, to the crotch, back, or other area. Such tubing need not be rigid and may collapse when air is not flowing through them. Further, multiple outlets may be incorporated into the bellows discharge distribution tubing which conveys air from the valving means into the product, so that air may be distributed in a particularly desired pattern within the product.

Figure 4:
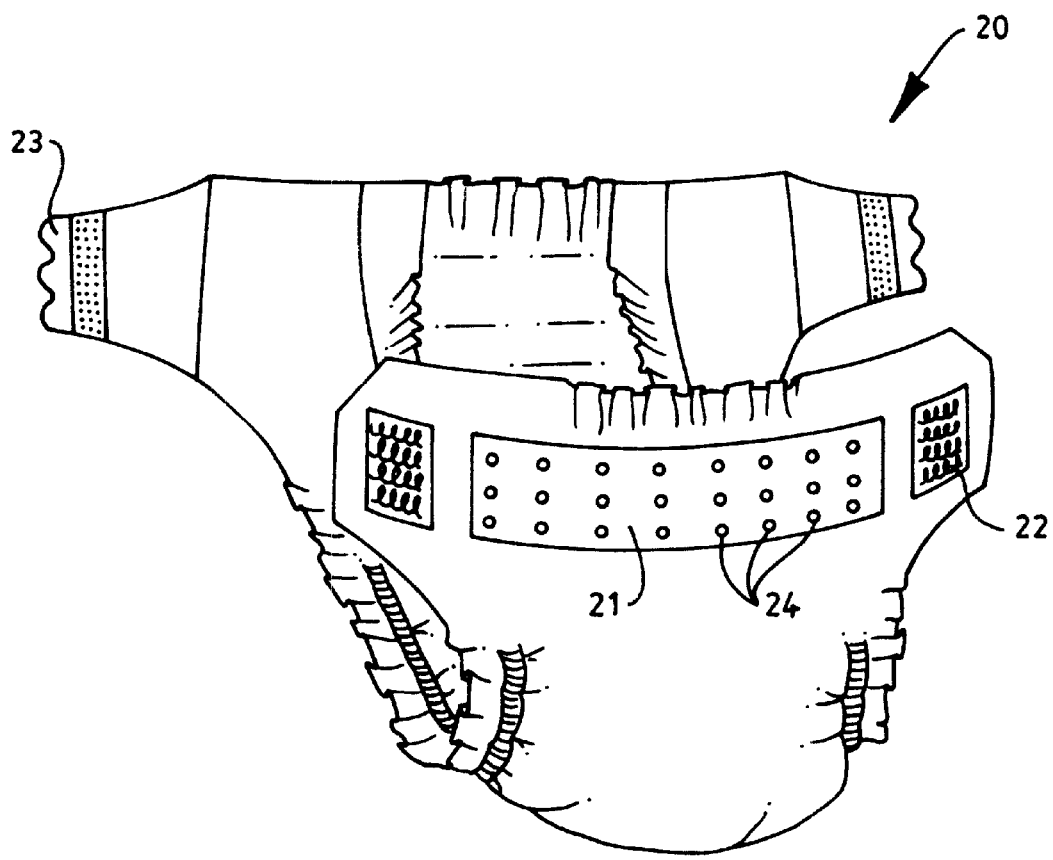
FIG. 4 shows an outside view of one example of a diaper with a bellows incorporated.
Figure 5:
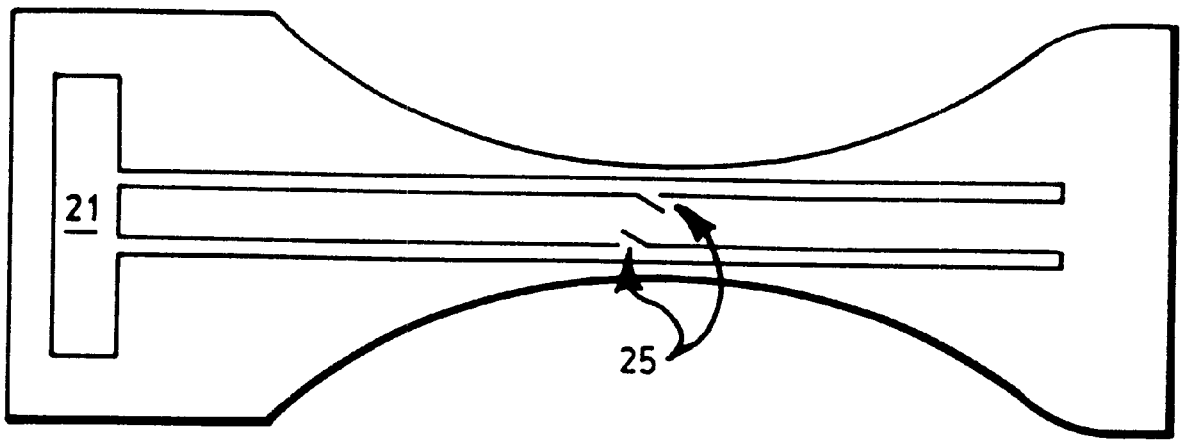
FIG. 5 shows a view of the inside of the diaper of FIG. 4 with components removed for clarity.

FIG. 4 shows an outside view of one example of a diaper 20 with a bellows 21 incorporated. The bellows 21 is located in the waist area of the diaper 20 between the attachment areas 22 for the "ears" 23 of the diaper 20. The intake valving 24 of the bellows 21 is located on the front of the diaper 20. FIG. 5 shows a view of the inside of a diaper showing the discharge valving 25 which is located on the inside (toward the wearer) of the product.

In use, in the case of a diaper for example, the waist bellows expands when the baby exhales and his/her stomach retracts, pulling air into a first one way (intake) valve and the bag from the outside. As the baby inhales, the expanding stomach pushes against the bellows and causes the bag to deflate. Since the intake valve will close as the stomach expands, the deflating bag pushes its air out of the second one way (discharge) valve and into the diaper.

Figure 6:
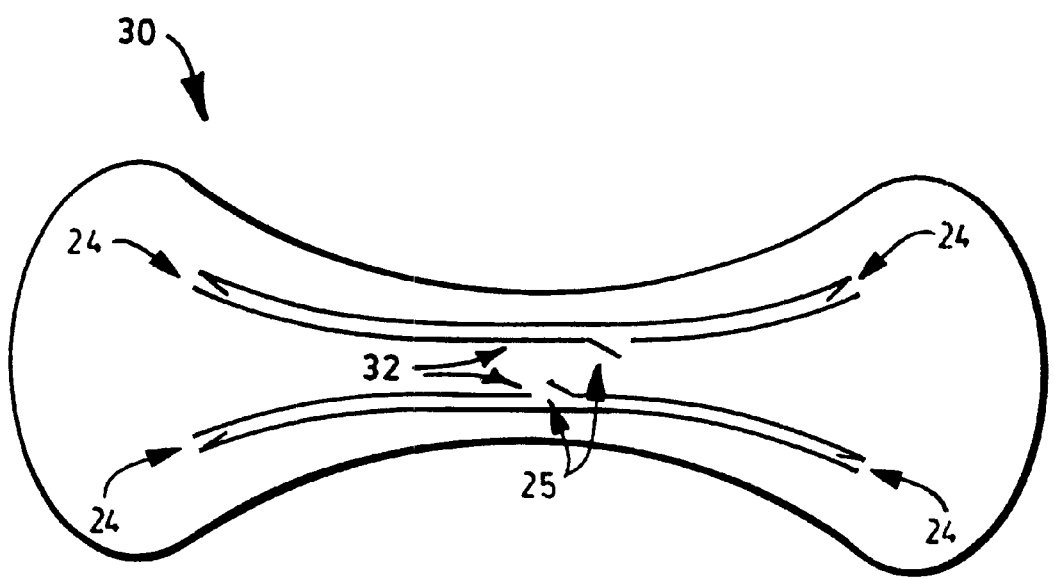
FIG. 6 shows a view of a sanitary napkin with components removed for clarity, having tubular bellows located on the periphery adjacent a wearer's legs.

In the leg location of a personal care product, for example, the bellows could be tubular in shape and arranged to run along the leg opening. This bellows could intake air through one way valves at either or both ends and discharge it through second one way valves into the central area of the product, and be activated by the normal leg movement of the wearer during walking. FIG. 6 shows a view of one example of a sanitary napkin 30 with a tubular bellows 32 incorporated in the peripheral position adjacent each leg. The intake valving 34 of the bellows 32 is located at both ends of the tubular bellows 32.

Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims.

It should further be noted that any patents, applications or publications referred to herein are incorporated by reference in their entirety.

What is claimed is:

1. A personal care product comprising a bellows adapted to be actuated by the normal movement of a wearer's body and discharge air into the personal care product in a region between a wearer's skin and the product in an area selected from the group consisting of a waist area, crotch area, back area and mixtures thereof, said bellows having sufficient resilience to spring back into shape and refill with air from outside of said product after being compressed by said movement; wherein said bellows comprises a first one way valve which intakes air from outside said product and a second one way valve which discharges air into said product in the region between the wearer's skin and the product.

2. The product of claim 1 wherein said bellows is located on a periphery of said product.

3. The product of claim 2 wherein said bellows is located in the waist area of said product.

4. The personal care product of claim 1 which is a diaper.

5. A personal care product comprising a bellows adapted to be actuated by the normal movement of a wearer's body and having sufficient resilience to spring back into shape and refill with air from outside of said product after being compressed by said normal movement, distribution means to convey air from the bellows into the product, and multiple outlets, so that air is distributed within the product in a region between a wearer's skin and the product, wherein said bellows comprise a first one way valve for intaking air from outside said personal care product and a second one way valve for discharging air in to a region between the wearer's skin and the personal care product.

6. The personal care product of claim 5 wherein said distribution means is selected from the group consisting of tubes and pipes.

7. The personal care product of claim 5 wherein said bellows includes an air containment bag and a resilient component.

* * * * *